United States Patent
Okuyama et al.

(10) Patent No.: US 9,610,058 B2
(45) Date of Patent: Apr. 4, 2017

(54) PORTABLE MEDICAL DIAGNOSTIC IMAGING APPARATUS AND COMMUNICATION CONTROL METHOD IN PORTABLE MEDICAL DIAGNOSTIC IMAGING APPARATUS

(71) Applicant: TOSHIBA MEDICAL SYSTEMS CORPORATION, Otawara-Shi (JP)

(72) Inventors: Satoshi Okuyama, Nasushiobara (JP); Takumi Yoshidome, Utsunomiya (JP); Megumu Fukuda, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 278 days.

(21) Appl. No.: 14/506,978

(22) Filed: Oct. 6, 2014

(65) Prior Publication Data

US 2015/0117426 A1   Apr. 30, 2015

(30) Foreign Application Priority Data

Oct. 30, 2013   (JP) ................................ 2013-225786

(51) Int. Cl.
| | | |
|---|---|---|
| *A61B 6/00* | (2006.01) | |
| *A61B 8/00* | (2006.01) | |
| *H04W 36/00* | (2009.01) | |
| *H04L 29/08* | (2006.01) | |

(52) U.S. Cl.
CPC .......... *A61B 6/563* (2013.01); *A61B 8/4472* (2013.01); *A61B 8/565* (2013.01); *H04W 36/0083* (2013.01); *A61B 8/4245* (2013.01); *H04L 67/12* (2013.01); *H04L 69/321* (2013.01)

(58) Field of Classification Search
None
See application file for complete search history.

(56) References Cited

U.S. PATENT DOCUMENTS

| | | | | |
|---|---|---|---|---|
| 2004/0151358 | A1* | 8/2004 | Yanagita | G06T 7/0012 382/132 |
| 2004/0259557 | A1* | 12/2004 | Bey | H04W 48/16 455/447 |
| 2010/0080476 | A1* | 4/2010 | Khorasani | G06F 19/321 382/235 |
| 2011/0003585 | A1* | 1/2011 | Wang | H04M 1/72583 455/418 |
| 2011/0249080 | A1* | 10/2011 | Choi | H04L 47/10 348/14.02 |
| 2013/0304489 | A1* | 11/2013 | Miller | G06Q 10/20 705/2 |

(Continued)

FOREIGN PATENT DOCUMENTS

JP   2013-111203   6/2013

*Primary Examiner* — Ayaz Sheikh
*Assistant Examiner* — Peter Chau
(74) *Attorney, Agent, or Firm* — Oblon, McClelland, Maier & Neustadt, L.L.P.

(57) ABSTRACT

A portable medical diagnostic imaging apparatus includes a wireless communication connection portion configured to connect to a network wirelessly, a signal strength obtaining portion configured to obtain signal strength of the wireless connection connected to the network, and a communication control portion configured to switch processing relating to data transmission in accordance with an obtained signal strength of the wireless connection.

10 Claims, 5 Drawing Sheets

(56) References Cited

U.S. PATENT DOCUMENTS

2014/0005506 A1\* 1/2014 Elghazzawi ......... A61B 5/0205
  600/324
2014/0153434 A1\* 6/2014 Kokovidis .............. H04L 67/12
  370/252

\* cited by examiner

|  | WIRED CONNECTION | NOT CONNECTED BY WIRE |
|---|---|---|
| WIRELESS CONNECTION (STRONG) | (WIRED) Storage/MPPS/MWM | (WIRELESS) Storage/MPPS/MWM |
| WIRELESS CONNECTION (WEAK) | (WIRED) Storage/MPPS/MWM | (WIRELESS) MPPS/MWM |
| NOT WIRELESSLY CONNECTED | (WIRED) Storage/MPPS/MWM | PROCESSING RESERVED |

PORTABLE MEDICAL DIAGNOSTIC IMAGING APPARATUS AND COMMUNICATION CONTROL METHOD IN PORTABLE MEDICAL DIAGNOSTIC IMAGING APPARATUS

CROSS-REFERENCE TO RELATED APPLICATION

This application is based upon and claims the benefit of priority from Japanese Patent Application No. 2013-225786, filed on Oct. 30, 2013, the entire contents of which are incorporated herein by reference.

FIELD

The present invention relates to a portable medical diagnostic imaging apparatus and a communication control method in the portable medical diagnostic imaging apparatus.

BACKGROUND

Recently, an image pickup apparatus with excellent portability has been in demand for efficient medical treatment at home. In a case where an inpatient is at hospital, the patient cannot move easily depending on the condition of a disease, and an image pickup apparatus moving around a hospital ward is in demand.

Actually, size reduction of the image pickup apparatus is in progress, and a portable apparatus has been realized in ultrasonic diagnostic apparatuses and X-ray apparatuses. For example, a portable medical diagnostic imaging apparatus relating to the ultrasonic diagnostic apparatus is realized.

An existing portable medical diagnostic imaging apparatus can be connected to a network by inserting a LAN (Local Area Network) cable to a network connector provided in the image pickup apparatus.

Since the portable medical diagnostic imaging apparatus has been realized recently, not only storing of picked-up images in the portable medical diagnostic imaging apparatus which picked up the images but also storing of the picked-up images in a medical image management system by transferring them via the network similarly to the existing apparatus is in demand.

Here, if the picked-up image picked up by the portable medical diagnostic imaging apparatus is to be transferred to and stored in the medical image management system via the network, it is necessary for the portable medical diagnostic imaging apparatus to be connected to the network via wireless connection without using the LAN cable in order to exert its superiority of portability.

However, in the case of the wireless connection, since signal strength of radio waves is different depending on a place where the portable medical diagnostic imaging apparatus is used, stable wireless communication cannot be conducted in some cases depending on the signal strength in the wireless connection. If a picked-up image is transferred to the medical image management system when stable wireless communication cannot be conducted, for example, image transfer might fail in the middle of the communication, and re-try might have to be made in some cases.

Thus, such a portable medical diagnostic imaging apparatus is in demand that, if stable wireless communication is possible, picked-up images are transferred, while if stable wireless communication is not possible, processing other than image transfer processing and applying a light load to the network is executed while the user is moving.

DETAILED DESCRIPTION

A portable medical diagnostic imaging apparatus and a communication control method in the portable medical diagnostic imaging apparatus of this embodiment will be explained by referring to the attached drawings.

The portable medical diagnostic imaging apparatus according to this embodiment includes, in order to solve the above-described problems, a wireless communication connection portion configured to connect to a network wirelessly, a signal strength obtaining portion configured to obtain signal strength of the wireless connection connected to the network, and a communication control portion configured to switch processing relating to data transmission in accordance with the signal strength of the obtained wireless connection.

The communication control method in the portable medical diagnostic imaging apparatus according to this embodiment is a communication control method in the portable medical diagnostic imaging apparatus which executes processing relating to data transmission via the network in order to solve the above-described problems, and the portable medical diagnostic imaging apparatus is provided with the wireless communication connection portion for wireless connection to the network and includes a signal strength obtaining step for obtaining the signal strength of the wireless connection connected to the network and a communication control step for switching the processing relating to the data transmission in accordance with the signal strength of the obtained wireless connection.

First Embodiment

Figure 1:
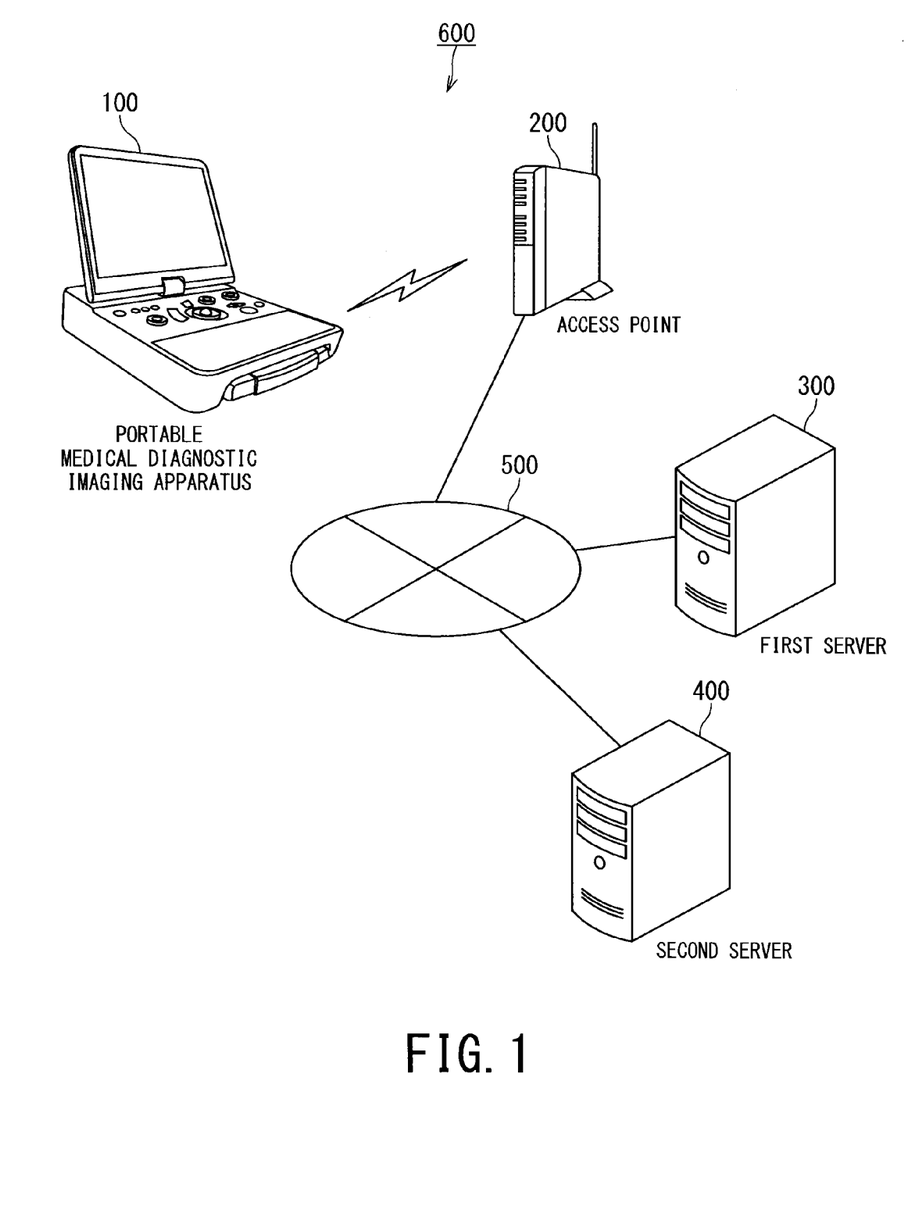
FIG. 1 is an outline configuration diagram illustrating an example of an outline configuration of an image pickup system provided with a portable medical diagnostic imaging apparatus according to a first embodiment.

An image pickup system 600 provided with a portable medical diagnostic imaging apparatus 100 according to a first embodiment will be explained below by referring to the attached drawings.

FIG. 1 is an outline configuration diagram illustrating an example of an outline configuration of the image pickup system 600 provided with the portable medical diagnostic imaging apparatus 100 according to the first embodiment.

As illustrated in FIG. 1, the image pickup system 600 includes the portable medical diagnostic imaging apparatus 100, an access point 200, a first server 300, a second server 400, a network 500 and the like.

The portable medical diagnostic imaging apparatus 100 is an image pickup apparatus for picking up an image of an object and corresponds to a portable ultrasonic diagnostic apparatus, an X-ray apparatus and the like. The ultrasonic diagnostic apparatus is a diagnostic imaging apparatus which applies ultrasonic waves to the object and can image its echo. The X-ray apparatus is an image pickup apparatus which irradiates X-rays to the object and can visualize the X-rays transmitted through the object by an X-ray detector. This embodiment can be applied to any image pickup apparatus as long as it is a portable image pickup apparatus capable of picking up an image of (photographing) the object.

The access point 200 is a radio-wave repeater for connecting the portable medical diagnostic imaging apparatus 100 to other terminals via a wireless LAN (Local Area Network). The access point 200 in this embodiment is configured to connect the portable medical diagnostic imaging apparatus 100 to the first server 300 and the second server 400 via the network 500.

The first server 300 and the second server 400 are image managing servers constituting a part of a medical image management system (PACS: Picture Archiving and Communication System). In this embodiment, this is a server for storing, browsing, and managing picked-up images (image data) obtained by picking up an image of an object (patient) by using the portable medical diagnostic imaging apparatus 100.

The network 500 is a network for connecting each apparatus connected to the image pickup system 600 to each other.

The portable medical diagnostic imaging apparatus 100 according to this embodiment is an image pickup apparatus provided with an image pickup function such as ultrasonic waves, X-rays and the like including a wireless communication connection portion for connection to the network 500 wirelessly, a signal strength obtaining portion for obtaining signal strength of the wireless connection connected to the network 500, and a communication control portion for switching processing relating to data transmission in accordance with the signal strength of the obtained wireless connection.

Figure 2:
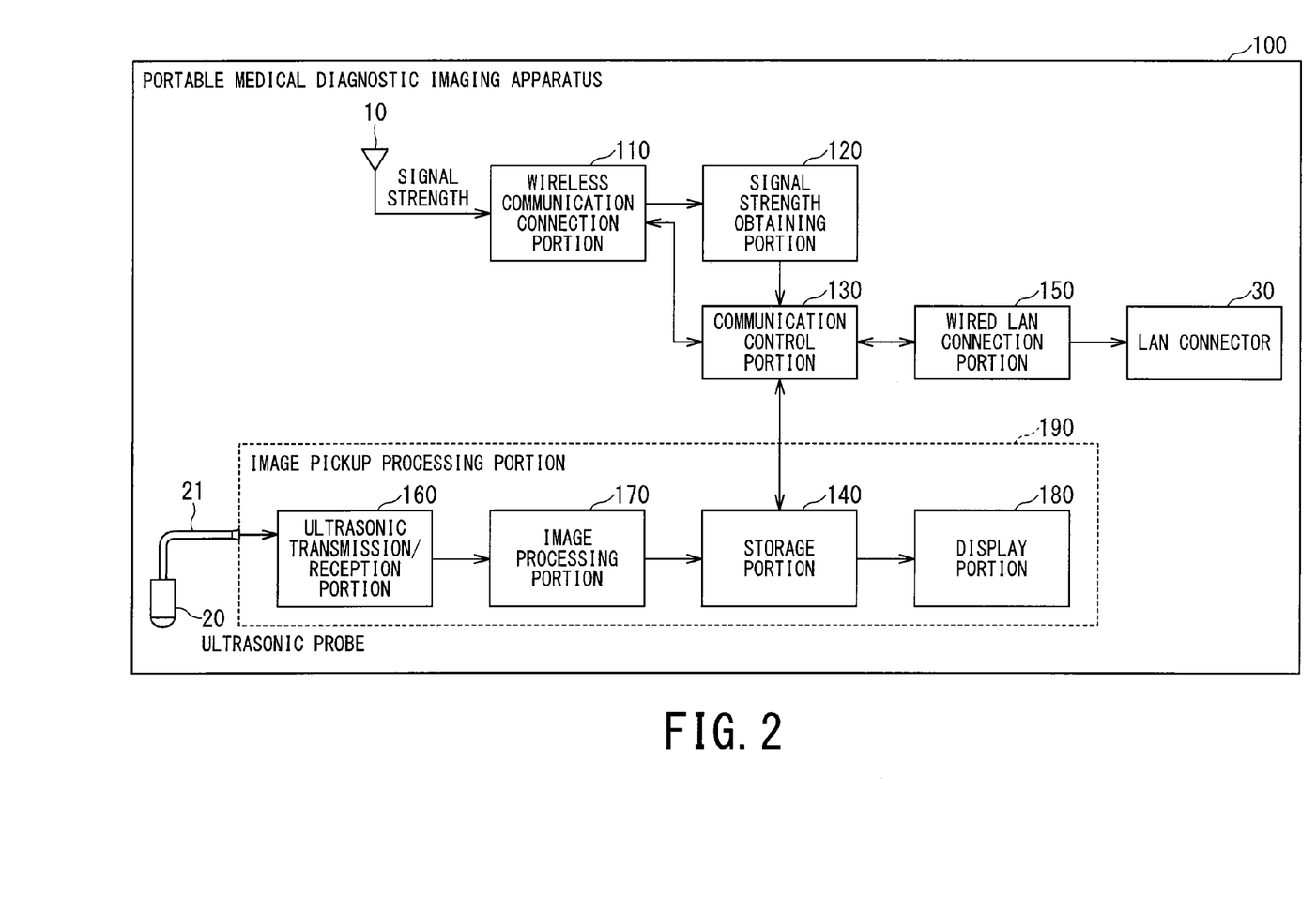
FIG. 2 is a functional block diagram illustrating a function of the portable medical diagnostic imaging apparatus according to the first embodiment.

FIG. 2 is a functional block diagram illustrating a function of the portable medical diagnostic imaging apparatus 100 according to the first embodiment.

As illustrated in FIG. 2, this portable medical diagnostic imaging apparatus 100 includes an antenna 10, a wireless communication connection portion 110, a signal strength obtaining portion 120, a communication control portion 130, a wired LAN connection portion 150, a LAN connector 30, an ultrasonic probe 20, a probe cable 21, an image pickup processing portion 190 and the like. The image pickup processing portion 190 includes an ultrasonic transmission/reception portion 160, an image processing portion 170, a storage portion 140, a display portion 180 and the like.

The antenna 10 is configured to transmit a transmission signal from the portable medical diagnostic imaging apparatus 100 to the access point 200 and to receive a reception signal from the access point 200. The transmission signal and the reception signal are configured to transmit/receive data by using radio waves.

The wireless communication connection portion 110 is an interface portion for connection to the network 500 wirelessly. The wireless communication connection portion 110 is configured to be able to connect to the network 500 by conducting wireless communication with the access point 200 via the antenna 10.

The signal strength obtaining portion 120 is configured to obtain signal strength of wireless connection between the portable medical diagnostic imaging apparatus 100 and the access point 200 connected to the network 500.

The communication control portion 130 is configured to switch processing relating to data transmission in accordance with the signal strength of the wireless connection obtained by the signal strength obtaining portion 120.

Here, the processing relating to data transmission includes first data transmission processing with a large transmission amount and second data transmission processing with a small transmission amount. If the signal strength of the wireless connection is strong, the communication control portion 130 is configured to switch the processing relating to the data transmission so as to execute both the first data transmission processing with the large transmission amount and the second data transmission processing with the small transmission amount (this is also called image data transmission processing), while if the signal strength of the wireless connection is weak, the communication control portion 130 is configured to switch the processing relating to the data transmission so as to execute only the second data transmission processing with the small transmission amount (this is also called management data transmission processing).

If the signal strength of the wireless connection is weak, the communication control portion 130 can switch the processing relating to the data transmission so as to stop the first data transmission processing and execute the second data transmission processing.

The wired LAN connection portion 150 has a connector to which the LAN cable is inserted and is configured to be able to connect to another network equipment when the LAN cable is inserted.

The LAN connector 30 is a connector to be connected in a wired manner to the network 500 and is connected to a connector provided on a wall of a consultation room or a wall of a ward, for example.

The ultrasonic probe 20 is configured to be brought into contact with a surface of the object and to transmit/receive ultrasonic waves while moving. Specifically, a plurality of ultrasonic oscillators are arranged on a tip end portion of the ultrasonic probe 20, the tip end portion is brought into contact with a photographing target of the object and the ultrasonic waves are transmitted/received. Moreover, the ultrasonic probe 20 is connected to the image pickup processing portion 190 via the probe cable 21.

The ultrasonic transmission/reception portion 160 of the image pickup processing portion 190 is composed of a transmission portion and a reception portion, supplies an electric signal to the ultrasonic probe 20 via the probe cable 21, and generates ultrasonic waves and moreover, it has a function of receiving an ultrasonic reception signal (echo signal) received by the ultrasonic probe 20 via the probe cable 21.

The image processing portion 170 includes a function of applying predetermined image processing to the reception signal of the ultrasonic waves received by the ultrasonic probe 20 and generating an ultrasonogram. Moreover, the image processing portion 170 is composed of a re-configuration portion and an image data specifying portion. The re-configuration portion is configured to associate information (positional data) relating to a position and an attitude obtained by a magnetic sensor (positional sensor) with the generated ultrasonogram and to reconfigure the image data on the basis of the generated ultrasonogram. The image data includes both videos and still images.

The storage portion 140 is a storage portion constituting a storage memory and is composed of a RAM (Random Access Memory), a hard disk and the like. The storage portion 140 stores image data reconfigured by the image processing portion 170.

The image data stored in the storage portion 140 is subjected to image transfer processing (Storage) to be transferred to the first server 300 and the second server 400, for example.

Moreover, the storage portion 140 is configured to store various types of information relating to modality worklist management (MWM) indicating a schedule of inspection by image pickup and a modality performed procedure step (MPPS) notifying a performance situation of the inspection by image pickup.

Here, the Storage, the MWM, and the MPPS are kinds of processing (services) standardized by DICOM (Digital Imaging and Communications in Medicine). The DICOM is a standard for applying processing specified in conformity to a function to medical image information. Moreover, the Storage, the MWM, and the MPPS are processing relating to the data transmission, respectively.

Specifically, the Storage is processing in which the communication control portion 130 transfers the image data stored in the storage portion 140 to the first server 300 or the second server 400 set in advance via the network 500.

The MPPS is processing of transmitting a performance situation of an inspection of the portable medical diagnostic imaging apparatus 100 to a radiology information system (RIS) (not shown). For example, start of the inspection and performance of the inspection are transmitted as a state of ongoing, and when the inspection is completed, a state of end is transmitted to the RIS via the network 500.

The MWM is processing of inquiring the RIS about an inspection schedule from the portable medical diagnostic imaging apparatus 100 via the network 500 before conducting an inspection and obtaining the worklist.

As described above, the first data transmission processing corresponds to data transmission processing of medical images with the large transmission amount, and the second data transmission processing corresponds to the data transmission processing of information relating to the worklist with the small transmission amount.

This embodiment is not limited to the processing specified by the DICOM but may be processing relating to information specified by a standard protocol for medical information exchange (HL7: Health Level Seven) and the like, for example. In this case, processing relating to the data transmission can be switched by classifying the medical information specified by the HL7 into the first data transmission processing or the second data transmission processing in accordance with the transmission amount.

Moreover, by classifying the medical information specified by the HL7 into the second data transmission processing, the medical information and the worklist specified by the DICOM can be used as work management information, for example.

The display portion 180 is composed of a liquid crystal display, a monitor and the like. The display portion 180 has a function of displaying the image data stored in the storage portion 140 and displaying a notification indicating a state of progress of the MPPS and a reservation situation of the MWM.

The portable medical diagnostic imaging apparatus 100 according to this embodiment is characterized by providing the wireless communication connection portion 110, the signal strength obtaining portion 120, the communication control portion 130, and the storage portion 140 in an image pickup apparatus provided with an image pickup function by ultrasonic waves or X-rays and also by including a function as an information processing device such as a CPU (Central Processing Unit) controlling processing and a ROM (Read Only Memory) storing a program.

The communication control portion 130 of the portable medical diagnostic imaging apparatus 100 according to this embodiment is configured to switch processing relating to data transmission between the processing relating to the data transmission such that, if the signal strength of the wireless connection is strong, the Storage corresponding to the first processing with the large transmission amount and the MWM and the MPPS corresponding to the second processing with the small transmission amount are executed (image data transmission processing) among the services specified in the DICOM standards, while if the signal strength of the wireless connection is weak, the MWM or the MPPS corresponding to the second processing with the small transmission amount is executed (management data transmission processing) among the services specified in the DICOM standards.

Figure 3:
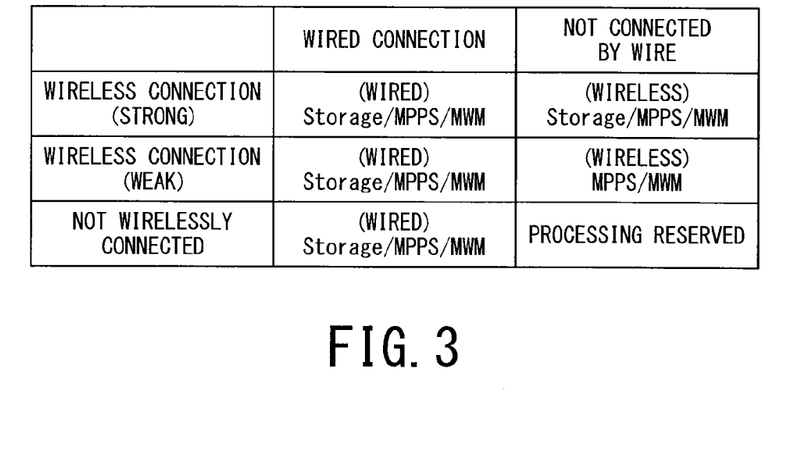
FIG. 3 is a control table illustrating a control method of switching processing relating to data transmission in accordance with a situation of a line by a communication control portion of the portable medical diagnostic imaging apparatus according to the first embodiment.

FIG. 3 is a control table illustrating a control method in which the communication control portion 130 of the portable medical diagnostic imaging apparatus 100 according to the first embodiment switches the processing relating to the data transmission in accordance with a situation of a line.

As illustrated in FIG. 3, this control table has a column for wired connection and a column of wired service interruption indicating that the wired connection is not possible (unconnected, for example). In the case of the wired connection, the communication control portion 130 is described to execute all the processing of the Storage, the MPPS, and the MWM regardless of the strength of the signal of wireless connection.

On the other hand, if the wired connection is not possible (wired service interruption), the communication control portion 130 is described to switch the processing relating to the data transmission so that, if the signal strength of the wireless connection is strong (wireless connection (strong)), the Storage with the large transmission amount (first data transmission processing) and the MPPS and the MWM with the small transmission amount (second data transmission processing) are executed, while if the signal strength of the wireless connection is weak (wireless connection (weak)), only the MPPS and the MWM with the small transmission amount (second data transmission processing) is executed.

In this embodiment, since the Storage with the large transmission amount has a large load applied to the network 500, while the MPPS and the MWM with the small transmission amount has a small load applied to the network 500, the processing relating to the data transmission is configured to be switched in accordance with the signal strength of the wireless connection.

In FIG. 3, if the signal strength of the wireless connection is strong, the Storage, the MPPS, and the MWM can be processed at the same time and thus, it is described as Storage/MWM/MPPS with the meaning that they are all executed. Moreover, in the case of wireless service interruption indicating that the wired connection is not possible and the wireless connection is not connected, it is described that service processing with the DICOM standard is reserved.

(Service Changing Processing)

Figure 4:
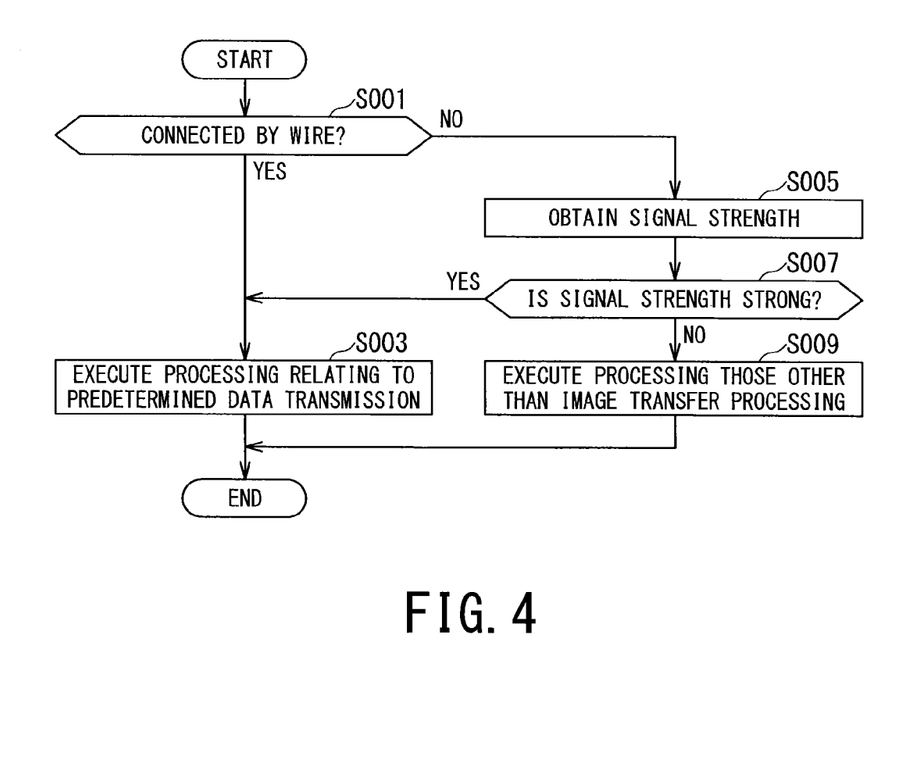
FIG. 4 is a flowchart illustrating service change processing in which the portable medical diagnostic imaging apparatus according to the first embodiment transfers image data in accordance with signal strength of wireless connection after the image data of an object is generated by using an ultrasonic probe.

Subsequently, service changing processing in which the portable medical diagnostic imaging apparatus 100 according to this embodiment changes a service in the wireless connection via the network 500 will be explained.

FIG. 4 is a flowchart illustrating the service changing processing in which, after the portable medical diagnostic imaging apparatus 100 according to this embodiment generates image data of the object by using the ultrasonic probe 20, the image data is transferred in accordance with the signal strength of the wireless connection. In FIG. 4, reference numerals with S indicate steps in the flowchart.

First, the portable medical diagnostic imaging apparatus 100 determines by the communication control portion 130 whether the connector provided on the wall of the consultation room or the wall of the ward and the LAN connector 30 are connected by the LAN cable and connected by wire to the network 500 or wirelessly connected to the access point 200 by the wireless communication connection portion 110 and the like (Step S001).

If the portable medical diagnostic imaging apparatus 100 is connected by wire by the LAN cable (YES at Step S001), wired connection to the network 500 is established and thus, the communication control portion 130 determines that the processing relating to the predetermined data transmission specified in the DICOM can be stably executed and executes the processing relating to the predetermined data transmission (Step S003).

Specifically, in the case of the processing relating to the predetermined data transmission described in FIG. 3 in the wired connection, for example, it is described that any of the Storage, the MPPS, and the MWM is executed, and the communication control portion 130 executes all the processing of the Storage, the MPPS, and the MWM.

In the Storage processing, the communication control portion 130 transfers the image data stored in the storage portion 140 to the first server 300 and the second server 400 set in advance via the network 500.

In the MPPS processing, the communication control portion 130 transmits the execution situation of the inspection of the portable medical diagnostic imaging apparatus 100 to the RIS (not shown). For example, the start of the inspection and the performance of the inspection are considered to be a state of ongoing, and a state of end is transmitted to the RIS via the network 500 when the inspection is completed.

In the MWM processing, the communication control portion 130 makes an inquiry about the inspection schedule with the RIS from the portable medical diagnostic imaging apparatus 100 via the network 500 before the inspection and obtains a worklist from the RIS.

When the processing relating to the predetermined data transmission at Step S003 is completed, the communication control portion 130 finishes the service changing processing.

On the other hand, if the portable medical diagnostic imaging apparatus 100 is not connected by wire by the LAN cable (NO at Step S001), the communication control portion 130 obtains the signal strength of the wireless connection between the portable medical diagnostic imaging apparatus 100 and the access point 200 from the signal strength obtaining portion 120 (Step S005).

The communication control portion 130 determines whether the signal strength of the wireless connection obtained from the signal strength obtaining portion 120 is strong or not (Step S007), and if the signal strength is strong (YES at Step S007), the communication control portion 130 executes the processing relating to the predetermined data transmission (all the processing of Storage/MPPS/MWM illustrated in FIG. 3, for example) (Step S003).

On the other hand if the obtained signal strength of the wireless connection is not strong (NO at Step S007), the communication control portion 130 determines that the signal strength of the wireless connection is weak and executes the processing (the MPPS/MWM with the small transmission amount illustrated in FIG. 3, for example) other than the Storage (image transfer processing) with the large transmission amount (Step S009).

The communication control portion 130 has a predetermined threshold value for making strength determination of the wireless connection (−55 dBm, for example), and if the signal strength of the wireless connection is at the predetermined threshold value or less, it is determined that the signal strength of the wireless connection is weak, while if the signal strength of the wireless connection is larger than the predetermined threshold value, it is determined that the signal strength of the wireless connection is strong.

As described above, the portable medical diagnostic imaging apparatus 100 according to this embodiment can switch the processing relating to the predetermined transmission on the basis of the signal strength of the wireless connection at the access point 200 and the portable medical diagnostic imaging apparatus 100.

As a result, the portable medical diagnostic imaging apparatus 100 according to this embodiment can execute the processing of the MPPS and the MWM without executing the Storage if the signal strength of the wireless connection at the access point 200 and the portable medical diagnostic imaging apparatus 100 is weak and thus, a transfer error of a picked-up image by the Storage can be avoided, and notification (MPPS) of the image pickup state and the image pickup completion and obtainment (MWM) of reservation information for image pickup by the portable medical diagnostic imaging apparatus 100 can be executed even in movement during doctor's hospital rounds and home healthcare.

As described above, the portable medical diagnostic imaging apparatus 100 according to this embodiment can transfer picked-up images when stable wireless communication can be conducted, while if stable wireless communication cannot be conducted, the portable medical diagnostic imaging apparatus 100 can execute data transfer processing with the small transmission amount which is the processing other than the image transfer processing while the user is moving.

In this embodiment, the communication control portion 130 obtains the signal strength of the wireless connection from the access point 200 and determines whether the signal strength is strong or weak on the basis of the predetermined threshold value. Moreover, in this embodiment, in the strength determination of the wireless connection, different threshold values may be provided for each switching between strong and weak signal strengths so that frequent switching is suppressed.

Figure 5:
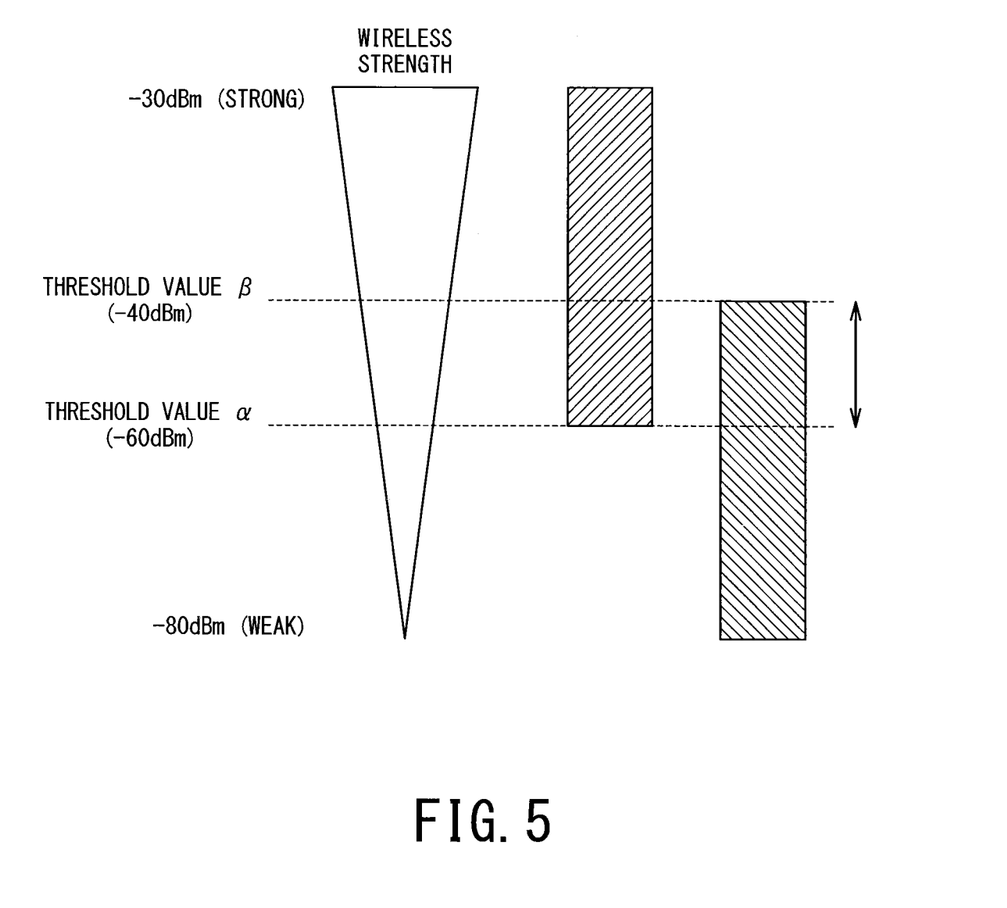
FIG. 5 is an explanatory diagram for explaining setting of two threshold values and switching between strong and weak in strength determination of wireless connection of the communication control portion.

FIG. 5 is an explanatory diagram for explaining the switching between strong and weak by providing the two threshold values in the strength determination of the wireless connection of the communication control portion 130.

As illustrated in FIG. 5, it is configured that, when the signal strength of the wireless connection becomes less than a threshold value α (−60 dBm as a first threshold value, for example) smaller than the predetermined threshold value (−55 dBm), the communication control portion 130 determines that the signal strength is weak, while if the signal strength of the wireless connection exceeds a threshold value β (−40 dBm as a second threshold value, for example), larger than the predetermined threshold value, the communication control portion 130 determines that the signal strength is strong.

As a result, if the signal strength of the wireless connection lowers from a strong state to less than the threshold value α, the communication control portion 130 determines that the signal strength is weak, reserves (stops) the Storage processing and switches the processing relating to transmission so that the processing other than the Storage is executed. On the other hand, if the signal strength of the wireless connection exceeds the threshold value β from the weak state, the communication control portion 130 determines that the signal strength is strong and switches the processing relating to transmission so that the Storage processing which has been reserved (stopped) is executed.

In this case, if the signal strength of the wireless connection is located between the threshold value α (first threshold value) and the threshold value β (second threshold value), the communication control portion 130 can maintain the state of the processing relating to data transmission.

As described above, the communication control portion 130 can suppress frequent switching involved with a change of the signal strength by making strength determination of the wireless connection by using the two threshold values in switching of the processing relating to transmission.

Moreover, if the signal strength of the wireless connection is at the predetermined threshold value or less (NO at Step S007), the communication control portion 130 determines that the signal strength of the wireless connection is weak, but this embodiment is not limited to that. For example, a threshold value for determining service interruption of the wireless connection is further provided, and if the signal strength of the wireless connection is determined by the threshold value to be service interruption, the communication control portion 130 may reserve (stop) the processing at Step S009.

As a result, the processing of the MPPS and the MWM (second data transmission processing) can be stopped under a condition different from that of the Storage processing (first data transmission processing).

Moreover, even if the signal strength of the wireless connection is determined to be weak (NO at Step S007), the communication control portion 130 may obtain the signal strength of the wireless connection at the portable medical diagnostic imaging apparatus 100 and the access point 200 from the signal strength obtaining portion 120 at a predetermined time interval (10-second interval, for example) without executing the processing at Step S009 immediately (Step S005).

In this case, even if the signal strength of the wireless connection is determined to be weak, the communication control portion 130 can wait for determination that the signal strength of the wireless communication is strong and thus, the processing relating to the predetermined data transfer at Step S003 can be executed.

Moreover, in this case, obtainment of the signal strength of the wireless connection at Step S005 is not limiting, and for example, the communication control portion 130 may return to Step S001, may determine whether or not the portable medical diagnostic imaging apparatus 100 is connected by wire by the LAN cable and may wait for connection to the network 500.

Second Embodiment

In the first embodiment, the processing of the Storage, the MPPS, and the MWM is executed at Step S003. In the second embodiment, when the processing of data transmission (Storage) is to be executed, processing contents are configured to be changed on the basis of the type of a file (hereinafter referred to as a type of an image) and a file size of the image.
(File Type Changing Processing)

Figure 6:
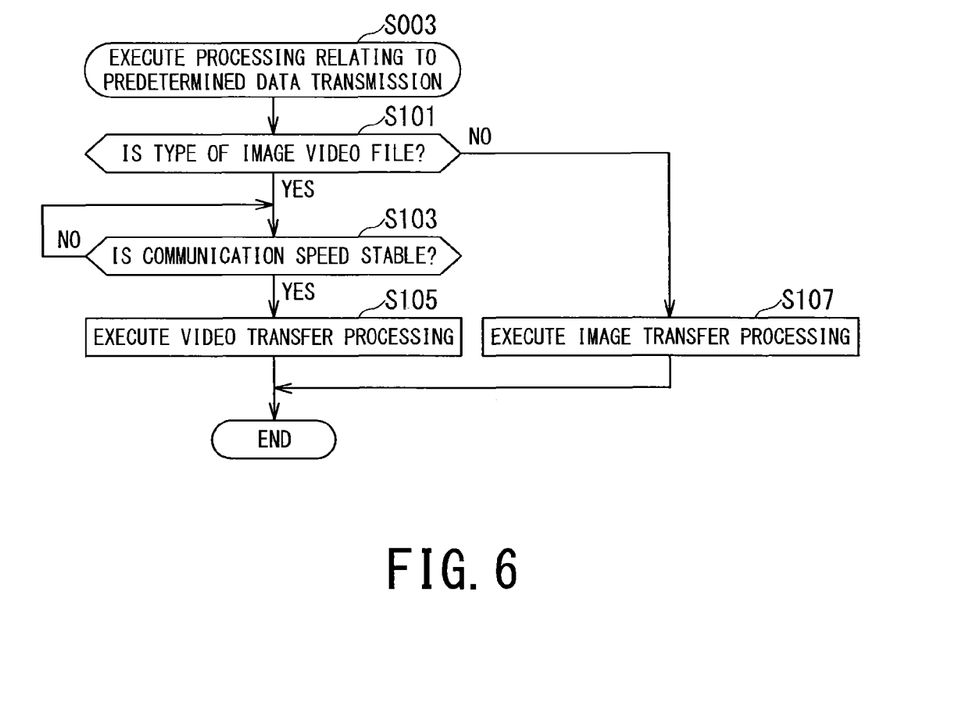
FIG. 6 is a flowchart illustrating file type changing processing for switching processing of data transmission in accordance with a type of an image when the portable medical diagnostic imaging apparatus according to a second embodiment executes predetermined processing contents.

FIG. 6 is a flowchart illustrating file type changing processing for switching the processing of data transmission in accordance with a type of an image when the portable medical diagnostic imaging apparatus 100 according to the second embodiment executes predetermined processing contents.

When the communication control portion 130 executes the storage as processing of the predetermined data transmission at Step S003, the communication control portion 130 determines the type of an image (Step S101) and if the type of the image is a video file (AVI (Audio Video Interleave), for example) (YES at Step S101), the communication control portion 130 determines whether the communication speed between the portable medical diagnostic imaging apparatus 100 and the other server (the first server 300 or the second server 400, for example) is stable or not (Step S103).

If the communication speed between the portable medical diagnostic imaging apparatus 100 and the other server (the first server 300, for example) is stable (when the effective communication speed is 30 Mbps or faster, for example) (YES at Step S103), the communication control portion 130 executes video transfer processing to the video file (Step S105), transfer the video file to the first server 300 via the network 500 and then, finishes the file type changing processing.

On one hand, if the communication speed between the portable medical diagnostic imaging apparatus 100 and the first server 300 is not stable (when the effective communication speed is 5 Mbps, for example) (NO at Step S103), the communication control portion 130 waits until the communication speed becomes stable at a predetermined effective communication speed (30 Mbps, for example) or faster and then, executes video transfer processing for transferring the video file to the first server 300 (Step S105).

On the other hand, if the type of the image is not a video file at Step S101 (NO at Step S101), the communication control portion 130 determines that the type of the image is a picked-up image (image data) relating to a still image (SC: Secondary Capture), executes image transfer processing for transferring the picked-up image relating to the still image to the second server 400 via the network 500 (Step S107) and finishes the file type changing processing.

The picked-up image relating to the still image is a digital image picked up by the portable medical diagnostic imaging apparatus 100 and corresponds to digital images subjected to image processing or image editing or those made into files in conformity to the specification of the DICOM and the like.

Moreover, if a file capacity of the still image (a file size of the image) exceeds a predetermined capacity (50 MB, for example) at Step S107, the communication control portion 130 may wait until the communication speed between the portable medical diagnostic imaging apparatus 100 and the second server 400 becomes stable at a predetermined effective communication speed (30 Mbps, for example) or faster and then, execute the image transfer processing to the second server 400 similarly to Step S103.

As described above, since the communication control portion 130 according to the second embodiment can determine whether or not to execute the transfer processing between the portable medical diagnostic imaging apparatus 100 and the other server (the first server 300 or the second server 400 and the like, for example) on the basis of the type of the image or the file size of the image and execute the video image transfer processing or the image transfer processing, a transfer error when the Storage processing is executed to the picked-up image can be avoided.

Moreover, when the communication control portion 130 executes the Storage processing, if there is no response within a predetermined time (within 5 minutes, for example) from a connection destination via the network 500, it is determined to be timeout, and the ongoing processing may be interrupted. In this case, in the case of the wireless connection, for example, time of the timeout may be set longer than that of the wired connection.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A portable medical diagnostic imaging apparatus comprising:
    a wireless communication connection interface configured to connect to a network wirelessly;
    a memory circuit configured to store a program; and
    a processor configured, by executing the program, to:
    obtain a signal strength of wireless connection connected to the network; and
    switch processing relating to data transmission in accordance with the obtained signal strength of the wireless connection,
    in accordance with the obtained signal strength of the wireless connection, switch the processing relating to data transmission between (a) image data transmission processing for executing both data transmission processing of a medical image obtained by photographing an object and data transmission processing of work management information relating to an inspection and (b) management data transmission processing of stopping the data transmission processing of the medical image and executing the data transmission processing of the work management information.

2. The portable medical diagnostic imaging apparatus according to claim 1, wherein
    the processing relating to data transmission includes:
    at least one of a service specified in conformity to a function in a DICOM (Digital Imaging and Communications in Medicine) standard and processing relating to information specified in HL7 (Health Level Seven).

3. The portable medical diagnostic imaging apparatus according to claim 1, wherein
    the processing relating to data transmission includes first data transmission processing and second data transmission processing, a transmission amount of the first data transmission processing being larger than a transmission amount of the second data transmission processing; and
    the processor is configured to:
    execute both the first data transmission processing and the second data transmission processing when signal strength of the wireless connection is strong, and
    switch the processing relating to data transmission so as to stop the first data transmission processing and execute the second data transmission processing when the signal strength of the wireless connection is weak.

4. The portable medical diagnostic imaging apparatus according to claim 3, wherein
    the processing relating to data transmission is a service specified in conformity to a function in a DICOM (Digital Imaging and Communications in Medicine) standard;
    the first data transmission processing is data transmission processing of a medical image; and
    the second data transmission processing is data transmission processing of information relating to a worklist.

5. The portable medical diagnostic imaging apparatus according to claim 3, wherein
    when the signal strength of the wireless connection is less than a first threshold value, the processor is configured to determine that the signal strength is weak; and
    when the signal strength of the wireless connection exceeds a second threshold value, the processor is configured to determine that the signal strength is strong and switch the processing relating to data transmission.

6. The portable medical diagnostic imaging apparatus according to claim 5, wherein
    when the signal strength of the wireless connection is located between the first threshold value and the second threshold value, the processor is configured to maintain a state of the processing relating to data transmission.

7. The portable medical diagnostic imaging apparatus according to claim 1, wherein
    the data transmission processing of work management information is stopped under a condition different from the data transmission processing of the medical image.

8. The portable medical diagnostic imaging apparatus according to claim 1, wherein
    the processor is configured to determine whether or not to execute the processing relating to data transmission on the basis of a type of an image or a file size of the image when processing relating to data transmission of a medical image is to be executed.

9. The portable medical diagnostic imaging apparatus according to claim 1, wherein
    when processing relating to data transmission of a medical video file is to be executed, the processor is configured to transfer the medical video file when a communication speed with a server at a connection destination connected to the network is at a predetermined speed or faster.

10. A communication control method in a portable medical diagnostic imaging apparatus for executing processing relating to data transmission via a network, wherein
the portable medical diagnostic imaging apparatus includes a wireless communication connection interface configured to connect to the network wirelessly, the method comprising
obtaining a signal strength of a wireless connection connected to the network; and
in accordance with the obtained signal strength of the wireless connection, switching the processing relating to data transmission between (a) image data transmission processing for executing both data transmission processing of a medical image obtained by photographing an object and data transmission processing of work management information relating to an inspection and (b) management data transmission processing of stopping the data transmission processing of the medical image and executing the data transmission processing of the work management information.

* * * * *